(12) United States Patent
Chava et al.

(10) Patent No.: US 7,884,214 B2
(45) Date of Patent: Feb. 8, 2011

(54) PROCESS FOR THE PREPARATION OF TELMISARTAN

(75) Inventors: Satyanarayana Chava, Secunderabad (IN); Seeta Ramanjaneyulu Gorantla, Secunderabad (IN); Sai Prasanna Bhagya Lakshmi Ginjupalli, Secunderabad (IN)

(73) Assignee: Matrix Laboratories Limited, Secunderabad (IN)

( * ) Notice: Subject to any disclaimer, the term of this patent is extended or adjusted under 35 U.S.C. 154(b) by 236 days.

(21) Appl. No.: 12/064,150

(22) PCT Filed: Jul. 19, 2006

(86) PCT No.: PCT/IN2006/000257

§ 371 (c)(1), (2), (4) Date: Jun. 18, 2008

(87) PCT Pub. No.: WO2007/010558

PCT Pub. Date: Jan. 25, 2007

(65) Prior Publication Data

US 2009/0023932 A1     Jan. 22, 2009

(30) Foreign Application Priority Data

Jul. 19, 2005   (IN) .......................... 957/CHE/2005

(51) Int. Cl.
*C07D 403/02*   (2006.01)
(52) U.S. Cl. .................................................. 548/305.4
(58) Field of Classification Search ............... 548/305.4
See application file for complete search history.

(56) References Cited

FOREIGN PATENT DOCUMENTS

WO    WO 2006/044754    *    4/2006

* cited by examiner

*Primary Examiner*—Yong Chu
*Assistant Examiner*—Valerie Rodriguez-Garcia
(74) *Attorney, Agent, or Firm*—Workman Nydegger

(57) ABSTRACT

The present invention encompasses a method for the preparation of Telmisartan comprises, through Telmisartan dihydrochloride comprises i) Condensing 4-Methyl-2-n-propyl-1H-benzimidazole-6-carboxylic acid with N-Methyl-O-phenylenediamine dihydrochloride to yields 4-methyl-6 (1-methyl benzimidazol-2-yl)-2-n-propyl 1H-benzimidazole ii) Treating 4-methyl-6-(1-methylbenzimidazol-2-yl)-2-n-propyl-1H-benzimidazole with 4'-(bromomethyl)-2-biphenyl-2-carboxylate in presence of a base in an organic solvent and isolating the ester as acid addition salt iii) Converting ester acid addition salt to Telmisartan dihydrochloride and iv) Converting Telmisartan dihydrochloride to Telmisartan.

6 Claims, No Drawings

PROCESS FOR THE PREPARATION OF TELMISARTAN

RELATED APPLICATIONS

The present application is a U.S. National Phase Application of International Application PCT/IN2006/000257 (filed: Jul. 19, 2006) which claims the benefit of Indian Application No. 957/CHE/2005 (filed Jul. 19, 2005), both of which are herein incorporated by reference in their entirety for all purposes.

The present invention relates to crystalline 4'-[[4-methyl-6-(1-methyl-1H-benzimidazol-2-yl)-2-propyl-1H-benzimidazol-1-yl]methyl]biphenyl-2-carboxylic acid dihydro-chloride (Telmisartan dihydrochloride), process for its preparation from 2-Propyl-4-methyl-1H-benzimidazole-6-carboxylic acid and its use thereof for preparing 4'-[[4-methyl-6-(1-methyl-1H-benzimidazol-2-yl)-2-propyl-1H-benzimidazol-1-yl]methyl]biphenyl-2-carboxylic acid (Telmisartan) and its pharmaceutically acceptable salts.

BACKGROUND OF THE INVENTION

4'-[[4-methyl-6-(1-methyl-1H-benzimidazol-2-yl)-2-propyl-1H-benzimidazol-1-yl]methyl]biphenyl-2-carboxylic acid (Telmisartan) has the formula as given below

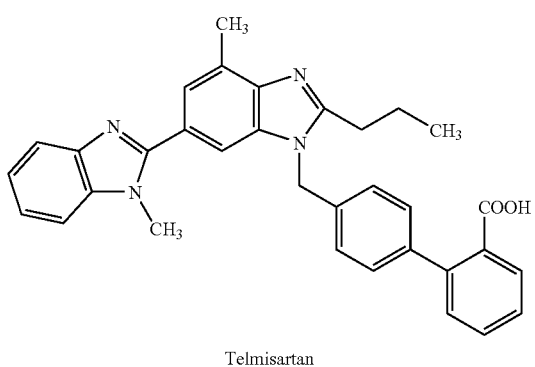

Telmisartan

Telmisartan and the physiologically acceptable salts are useful as angiotensin antagonists, particularly an angiotensin-II-antagonist, may be used to treat hypertension, cardiac insufficiency, to treat ischaemic peripheral circulatory disorders, myocardial ischaemia (angina), to prevent the progression of cardiac insufficiency after myocardial infarct, to treat diabetic neuropathy, glaucoma, gastrointestinal diseases and bladder diseases.

U.S. Pat. No. 5,591,762 discloses Telmisartan, methods for its preparation and methods of pharmaceutical formulations using Telmisartan. The process disclosed in U.S. Pat. No. 5,591,762 involves (Scheme-1)

i. Reacting 4-methyl-6(1-methylbenzimidazol-2-yl)-2-n-propyl-1H-benzimidazole with t-Butyl 4'-(bromomethyl)-2-biphenyl-2-carboxylate in the presence of an acid binding agent in a solvent or mixture of solvents.

ii. It further discloses the formation of a mixture of the 1 and 3 isomers and their separation by chromatography using a substrate such as silica gel or aluminum oxide to obtain t-Butyl-4'-[4-Methyl-6-(1-methyl-1H-benzimidazol-2-yl)-2-n-propyl-1H-benzimidazol-1-yl-methyl] biphenyl-2-carboxylate.

iii. Hydrolysis of the t-Butyl 4'-[4-Methyl-6-(1-methyl-1H-benzimidazol-2-yl)-2-n-propyl-1H-benzimidazol-1-yl-methyl]biphenyl-2-carboxylate with trifluoro acetic acid in dimethyl formamide followed by purification with silica gel column and crystallization.

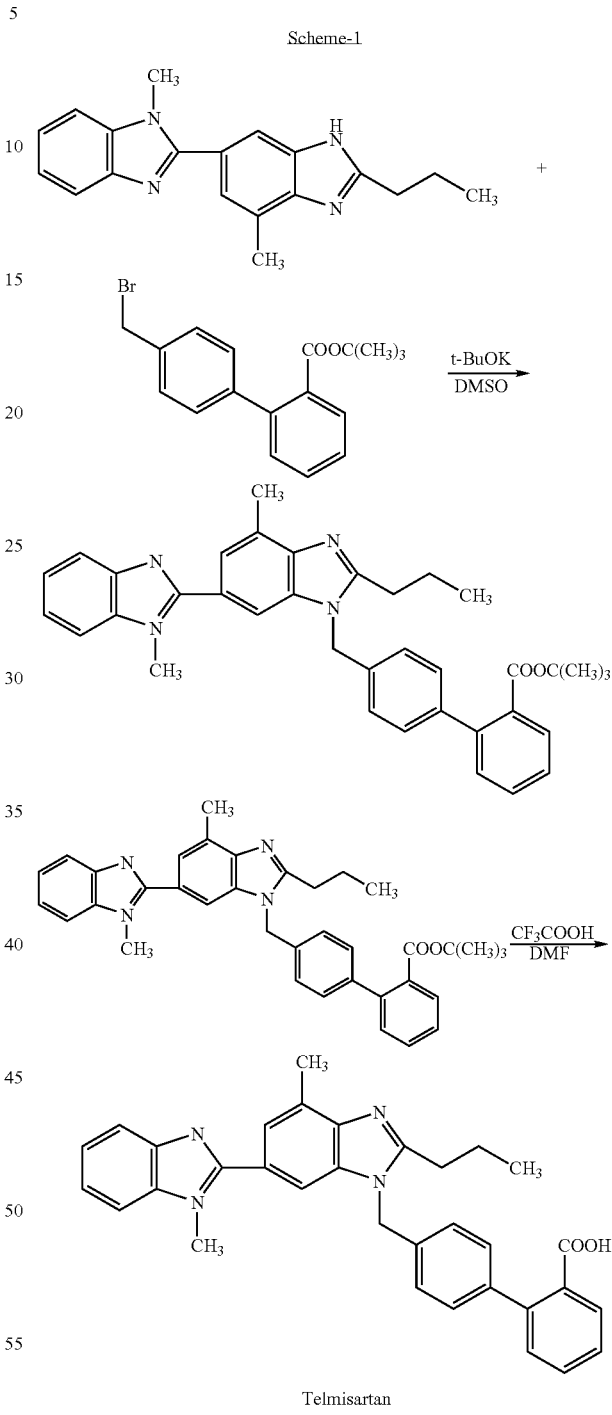

U.S. Pat. No. 6,358,986 discloses the form A, form B and mixtures of the polymorphs of Telmisartan. This patent also discloses that polymorphic form A, melts at 269±2° C., characteristic band at 815 cm$^{-1}$ in the IR spectrum is considered as prior art form. The polymorphic form B melts at 183±2° C. (by DSC), characteristic band at 830 cm$^{-1}$ in IR spectrum. The disclosed process for polymorphic form B and mixtures involves dissolving crude Telmisartan in a mixture of water, formic acid and organic solvents, at elevated temperature, and precipitating with a suitable base followed by drying under vacuum at 120-125° C. U.S. Pat. No. 6,358,986 further discloses that after centrifugation, the product begins to change to polymorphic form A depending on the temperature, pH, retention time and water content towards the end of the drying.

U.S. Pat. No. 6,737,432 disclosed crystalline sodium salt of Telmisartan characterized by melting point (245±5° C.), XRD, processes for preparation and use thereof for preparation of a pharmaceutical composition. It further discloses the solvates and hydrates of crystalline Telmisartan sodium. The disclosed process for preparation of Telmisartan sodium involves the reaction of sodium salts such as sodium hydroxide, sodium hydride, sodium carbonate, sodium bicarbonate or sodium alkoxides with Telmisartan in an organic aprotic solvent. The alternate process disclosed for preparation of Telmisartan sodium salt is by treatment of Telmisartan acid addition salts, hydrochloride salt with bases such as sodium hydroxide, sodium hydride, sodium carbonate, sodium bicarbonate or sodium alkoxides in a suitable solvent, may be water and/or a suitable alcohol mixed with an aprotic organic solvent by heating the mass along with charcoal to temperature to <40° C., filtering to remove the insolubles, distilling the solvent followed by azeotropic removal of solvent, left to crystallize, filteration, optionally washing with above mentioned aprotic solvent and drying.

The U.S. Pat. No. 6,737,432 further characterizes the Telmisartan hydrochloride, melting point 278° C., the disclosed process for preparation of Telmisartan hydrochloride involves the reaction of t-Butyl 4'-[4-Methyl-6-(1-methyl-1H-benzimidazol-2-yl)-2-n-propyl-1H-benzimidazol-1-yl-methyl]biphenyl-2-carboxylate with aqueous hydrochloric acid (37%) in glacial acetic acid by refluxing, partial removal of solvent by distillation, dissolution in water, charcoal treatment, crystallization by stirring for about 12 hrs at 23° C., filtration, washing with water, acetone and drying at about 60° C.

U.S. Pat. Application No. 2003/139608 disclosed and claimed the process for the preparation of pure 4-methyl-6(1-methyl benzimidazol-2-yl)-2-n-propyl-1H-benzimidazole by purifying the crude product obtained by reaction of 2-n-propyl-4-methyl-1H-benzimidazole-6-carboxylic acid on reaction with N-methyl-o-phenylenediamine preferably in the form of salt, by charcoal treatment of said crude reaction product.

The prior art processes discloses for preparation of Telmisartan involving the column chromatographic purifications of intermediate and/or final stage. The process disclosed for preparation of Telmisartan hydrochloride involves the usage, distillation of glacial acetic acid along with hydrochloric acid, which requires acid resistant equipment. Hence there is a need for a simple process for preparation of Telmisartan without involving the column chromatographic purifications and distillation of acids in various stages during the process.

SUMMARY OF THE INVENTION

The main object of the present invention is to provide an economic process for the preparation of Telmisartan.

Another object of the invention is to provide a process for the preparation of Telmisartan using its acid addition salts.

Another object of the invention is to provide a process for preparation of Telmisartan acid addition salts Another object of the invention is to provide a process for preparation of acid addition salts of Telmisartan esters Another object of the invention is to provide a process for preparation of Telmisartan using acid addition salts of Telmisartan esters Another object of the invention is to provide a process for preparation of acid addition salts of Telmisartan using acid addition salts of Telmisartan esters Yet another object of the invention is to provide a novel Telmisartan acid addition salts Yet another object of the invention is to provide novel acid addition salts of Telmisartan esters Accordingly in the present invention 4-Methyl-2-n-propyl-1H-benzimidazole-6-carboxylic acid with N-Methyl-o-phenylenediamine dihydrochloride in the presence of polyphosphoric acid (PPA) followed by purification gives 4-methyl-6(1-methyl benzimidazol-2-yl)-2-n-propyl 1H-benzimidazole which on condensation with 4'-(bromomethyl)-2-biphenyl-2-carboxylate esters in the presence of base followed by acidification gives 4'-[4-Methyl-6-(1-methyl-1H-benzimidazol-2-yl)-2-n-propyl-1H-benzimidazol-1-yl-methyl]biphenyl-2-carboxylate ester acid addition salt (acid addition salts of Telmisartan ester), on hydrolysis with hydrochloric acid gives the 4'-[4-Methyl-6-(1-methyl-1H-benzimidazol-yl)-2-n-propyl-1H-benzimidazol-1-yl-methyl]biphenyl-2-carboxylic acid dihydrochloride salt (Telmisartan dihydrochloride). Telmisartan dihydrochloride on treatment with a base in presence of suitable solvent gives the Telmisartan (Scheme-2).

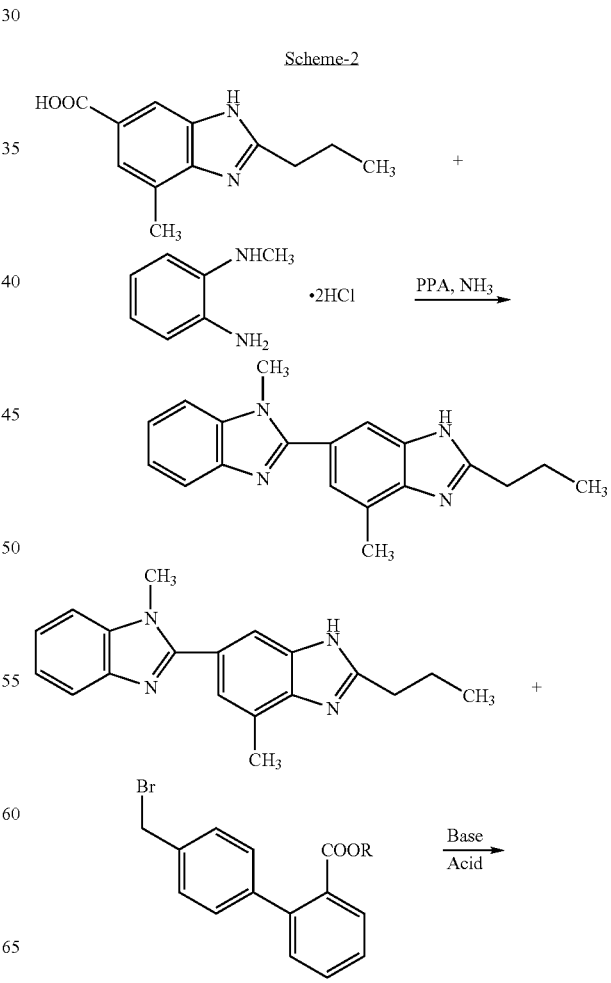

Scheme-2

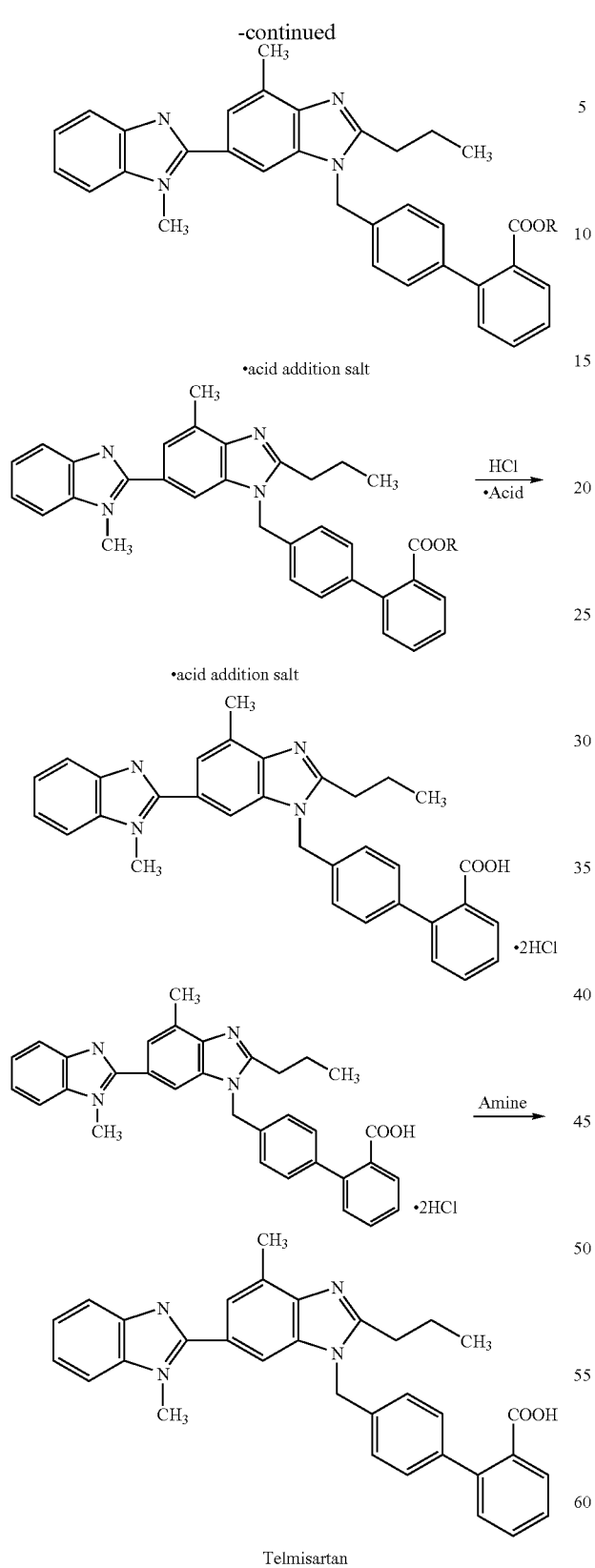

Telmisartan

The prepared intermediates, 4'-[4-Methyl-6-(1-methyl-1H-benzimidazol-2-yl)-2-n-propyl-1H-benzimidazol-1-yl-methyl]biphenyl-2-carboxylate ester acid addition salt (acid addition salts of Telmisartan ester), Telmisartan dihydrochloride are novel compounds, characterized, identified by chemical analysis. The prepared Telmisartan is in the polymorphic form of form A, identified by its characteristic melting point (DSC) and IR spectrum.

DETAILED DESCRIPTION OF THE INVENTION

Thus in accordance with the present invention preparation of Telmisartan comprises the following steps.

Condensing 4-Methyl-2-n-propyl-1H-benzimidazole-6-carboxylic acid with N-Methyl-o-phenylenediamine dihydrochloride in the presence of polyphosphoric acid (PPA) yields 4-methyl-6 (1-methyl benzimidazol-2-yl)-2-n-propyl 1H-benzimidazole Treating 4-methyl-6-(1-methyl benzimidazol-2-yl)-2-n-propyl-1H-benzimidazole with 4'-(bromomethyl)-2-biphenyl-2-carboxylate in presence of a base in an organic solvent followed by treatment with mineral acid yields acid addition salt of 4'-[4-Methyl-6-(1-methyl-1H-benzimidazol-2-yl)-2-n-propyl-1H-benzimidazol-1-yl-methyl]biphenyl-2-carboxylate ester Treating 4'-[4-Methyl-6-(1-methyl-1H-benzimidazol-2-yl)-2-n-propyl-1H-benzimidazol-1-yl-methyl]biphenyl-2-carboxylate ester acid addition salt with aqueous hydrochloric acid yields Telmisartan dihydrochloride Converting the Telmisartan dihydrochloride to Telmisartan In a specific embodiment, the present invention provides a process for the preparation of Telmisartan, which involves i. Suspending 4-Methyl-2-n-propyl-1H-benzimidazole-6-carboxylic acid in polyphosphoric acid and raising the temperature to 60° C. to 150° C., preferably to 70° C. to 120° C.

ii. Adding N-Methyl-O-phenylenediamine dihydrochloride is added preferably lot wise over 1 hr to 6 hrs at temperature of 60° C. to 150° C. preferably at 70° C. to 120° C.

iii. Maintaining the reaction mass for about 3 hrs to 15 hrs at temperature of 100° C. to 150° C. and cooling the mass to 60° C. to 90° C.

iv. Adding water (0.5 vol to 2 vol per mole of 4-Methyl-2-n-propyl-1H-benzimidazole-6-carboxylic acid) at about 60° C. to 100° C. followed by about 5 vol to 15 vol of water at temperature of about 25° C. to about 90° C.

v. Maintaining the reaction mass for 10 min and the pH is adjusted by addition of aqueous ammonia at about 25° C. to 65° C. and maintaining the reaction mass at 40° C.-60° C. for about 30 min to 90 min vi. Isolating the product and slurring the wet cake in water at about 35° C. to 60° C., and drying the product.

vii. Suspending the crude 4-methyl-6 (1-methyl benzimidazol-2-yl)-2-n-propyl 1H-benzimidazole is suspended in a lower alcohol; for example methanol, ethanol or isopropanol, preferably methanol, treating with activated charcoal and filtering the mass over hyflow viii. Adding water to the clear filtrate and maintaining the mass at 25° C. to reflux temperature of the solvent.

ix. Cooling the mass to 0° C. to 30° C., preferably 0 to 10° C., isolating and drying at 40° C. to 80° C. afforded the pure 4-methyl-6 (1-methyl benzimidazol-2-yl)-2-n-propyl 1H-benzimidazole Further reacting the resultant 4-methyl-6-(1-methyl benzimidazol-2-yl)-2-n-propyl-1H-benzimidazole with 4'-(bromomethyl)-2-biphenyl-2-carboxylate is carried out by i. Suspending 4-methyl-6 (1-methyl benzimidazol-2-yl)-2-n-propyl 1H-benzimidazole in an organic solvent such as acetone, methyl ethyl ketone, methyl isobutyl ketone, preferably acetone,
ii. Adding a base such as sodium hydroxide, potassium hydroxide,
iii. Cooling the mass to temperature of −10° C. to 30° C., preferably 0 to 10° C., addition of then maintaining the reaction mass at temperature of −10° C. to 30° C., preferably 0 to 10° C. for about 4 hrs to 10 hrs, preferably about 4 hrs to 8 hrs,
iv. Adding 4'-(bromomethyl)-2-biphenyl-2-carboxylate ester, such as methyl, tert butyl ester,
v. Maintaining the reaction mass at −10° C. to 30° C. preferably 0 to 10° C. for about 4 hr to 10 hrs, preferably 4 to 8 hrs
vi. Removing the solvent preferably under vacuum, adding a mixture of water, water immiscible solvent; for example methylene chloride, ethylene chloride or chloroform, preferably methylene chloride,
vii. Acidification with mineral acid; for example hydrochloric acid, hydrobromic acid, sulphuric acid or phosphoric acid, preferably hydrochloric acid to a pH of about 0.5 to 4.0,
viii. Separating the layers, optionally extracting the aqueous layer with the above water immiscible solvent, treating the organic layer with activated charcoal,
ix. Removal of solvent, addition of a ketone; for example acetone, methyl ethyl ketone or methyl isobutyl ketone, preferably acetone and adjusting the pH to 0.5 to 4.0 with the above mineral acid followed by maintaining the reaction mass at temperature of 20° C. to reflux temperature of solvent,
x. Isolation, washing the wet cake with water, followed by the above ketone and drying at temperature of 40° C. to 80° C. affords 4'-[4-Methyl-6-(1-methyl-1H-benzimidazol-2-yl)-2-n-propyl-1H-benzimidazol-1-yl-methyl]biphenyl-2-carboxylate ester acid addition salt. The acid addition salt is hydrobromide, hydrochloride, sulphate or phosphate.

Acid addition salts of 4'-[4-Methyl-6-(1-methyl-1H-benzimidazol-2-yl)-2-n-propyl-1H-benzimidazol-1-yl-methyl]biphenyl-2-carboxylate ester obtained above are found to be novel and hydrolysis of respective acid addition salts comprises i. Suspending the 4'-[4-Methyl-6-(1-methyl-1H-benzimidazol-2-yl)-2-n-propyl-1H-benzimidazol-1-yl-methyl]biphenyl-2-carboxylate ester acid addition salt in a water miscible solvent; for example acetone, methanol or ethanol,
ii. Addition of hydrochloric acid and maintaining the reaction mass at temperature of 30 to 75° C., preferably 45 to 65° C., for about 1 hr to 6 hrs, preferably for about 2 hrs to 4 hrs,
iii. Cooling the mass to a temperature of 10° C. to about 40° C., optionally maintaining for about 1 hr,
iv. Isolation, washing with water followed by water miscible solvent and drying at temperature of 40° C. to 75° C. gives the Telmisartan dihydrochloride.

The obtained Telmisartan dihydrochloride has the water content of below 3% and melting point of about 249±2° C. (DSC). Telmisartan dihydrochloride is further converted to Telmisartan by
i. Dissolving Telmisartan dihydrochloride in a lower alcohol; for example methanol, ethanol or propanol if required by heating, ii. Optionally treating with charcoal and removing the insolubles,
iii. Adjusting the pH of the reaction mass to 5.0 to 7.0 with a base preferably ammonia solution at temperature of 15 to 45° C.
iv. Maintaining the reaction mass at 40° C. to reflux temperature, for about 30 min to 90 min, cooling the mass to −10° C. to 25° C., maintaining for about 2 hrs to about 12 hrs,
v. Isolating, washing the wet cake with water, optionally with the above lower alcohol, drying at 60° C. to 90° C. gives the Telmisartan.

4-Methyl-2-n-propyl-1H-benzimidazole-6-carboxylic acid can be prepared by the prior art methods.

The invention is further illustrated with a few non-limiting examples

Example 1

Step-I: Preparation of 4-Methyl-6(1-methyl benzimidazol-2-yl)-2-n-propyl 1H-benzimidazole 4-Methyl-2-n-propyl-1H-benzimidazole-6-carboxylic acid (50 gms) is suspended in Poly phosphoric acid (300 gms), temperature is raised and maintained for 30 min at 70-75° C., N-Methyl-o-phenylenediamine dihydrochloride. (45 gms) is added lot wise over 2 hrs and maintained at temperature of 70-75° C. for 1 hr. The temperature of the reaction mass is raised and maintained for 10 hrs at 130-135° C. Mass temperature is cooled to 70° C., water (600 ml) is added slowly at temperature of 60-90° C. Temperature of the reaction mass is cooled to 30° C., pH is adjusted to 8.0-8.5 with aqueous ammonia solution. Temperature of the reaction mass is raised, maintained at 50-55° C. for 1 hr, filter the solid, wet cake is washed with hot water (200 ml) and unload the wet cake. The above wet cake suspended in water (900 ml), temperature is raised and mixed for 1 hr at 50-55° C. Filtered the solid, washed with hot water (100 ml) and dried the wet cake at temperature of 70-75° C. till constant weight. The above dry material is suspended in methanol (260 ml), and temperature is raised to 45-50° C., charcoal (6.5 gms) is added and mixed for about 30 min. Insolubles are filtered through hyflow bed, washed the bed with hot methanol (60 ml), collect and cooled the filtrate to 25° C. Water (160 ml) is added slowly to the filtrate at temperature of 25-35° C., Mass temperature is raised, maintained for 1 hr at reflux temperature. Reaction mass temperature is cooled, maintained for 2 hrs at 0-5° C. The solid obtained is filtered, wet cake is washed with methanol (60 ml), the wet cake is dried at temperature of 70-75° C. till becomes constant weight.

The dry weight of 4-Methyl-6(1-methyl benzimidazol-2-yl)-2-n-propyl 1H-benzimidazole is 54 gms (Yield 77.4%). Water content by KF is 5.85%.

Step-2: Preparation of tert Butyl 4'-[4-Methyl-6-(1-methyl-1H-benzimidazol-2-yl)-2-n-Propyl-1H-benzimidazol-1-yl-methyl]biphenyl-2-carboxylate hydrochloride 4-Methyl-6-(1-methyl benzimidazol-2-yl)-2-n-propyl 1H-benzimidazole (50 gms) is suspended in acetone (500 ml), aqueous potassium hydroxide solution (13.8 gms in 31.4 ml of water) is added and mixed for 30 min at temperature of 25-30° C. The mass is cooled, t-Butyl 4'-(bromomethyl)-2-biphenyl-2-carboxylate (50 gms) slowly added over 30 min and maintained the reaction mass at temperature of 0-5° C. for 6 hrs. The solvent is distilled off from the reaction mass at temperature below 50° C. under vacuum. Water (500 ml).

Methylene chloride (300 ml) is added to the residue and mixed for about 15 min. pH of the reaction mass is adjusted with hydrochloric acid to 1.8 at temperature of 20-25° C. Reaction mass is allowed to settle, layers are separated, aqueous layer is extracted with methylene chloride (100 ml). Combined organic layer is washed water (100 ml), treated with charcoal (5 gms) and dried the organic layer over anhydrous sodium sulphate (10 gms). Solvent is distilled off from the dried organic layer at temperature below 50° C. finally under vacuum. Acetone (100 ml) is added to the residue, mixed for about 10 min and solvent is distilled off under vacuum at temperature below 50° C. Acetone (300 ml) is added to the residue, cooled the mass to 30° C. and pH of the mass is adjusted to 2.8 with IPA HCl (about 2 ml). Temperature of reaction mass is raised, maintained for 1 hr at reflux temperature, cooled and maintained for 30 min at 25-30° C. Product is filtered, wet cake is washed with acetone (50 ml) and dried the wet cake at temperature of 60-70° C. till becomes constant weight.

The Dry weight of tert Butyl 4'-[4-Methyl-6-(1-methyl-1H-benzimidazol-2-yl)-2-n-propyl-1H-benzimidazol-1-yl-methyl]biphenyl-2-carboxylate hydrochloride is 73 gms (Yield: 73%). HCl content: 5.85% w/w Step-3: Preparation of 4'-[4-Methyl-6-(1-methyl-1H-benzimidazol-2-yl)-2-n-propyl-1H-benzimidazol-1-yl-methyl]biphenyl-2-carboxylic acid dihydrochloride (Telmisartan dihydrochloride)

Tert.Butyl-4'-[4-Methyl-6-(1-methyl-1H-benzimidazol-2-yl)-2-n-propyl-1H-benzimidazol-1-yl-methyl]biphenyl-2-carboxylate hydrochloride (50 gms) is suspended in acetone (250 ml) and hydrochloric acid (50 ml) is added. Temperature of the mass is raised, maintained at 50° C.-55° C. for 3 hrs, cooled and maintained at 25-30° C. for 2 hrs. Product is filtered; wet cake is washed with water (2×50 ml) and acetone (50 ml). Dried the wet cake at temperature 60° C.-65° C. till constant weight.

Dry weight of Telmisartan dihydrochloride is 44 gms (Yield: 90.8%)

HCl content: 11.89% w/w; Water content: 2.85%

Step-4: Preparation of 4'-[4-Methyl-6-(1-methyl-1H-benzimidazol-2-yl)-2-n-prop 1H-benzimidazol-1-yl-methyl]biphenyl-2-carboxylic acid (Telmisartan)

4'-[4-Methyl-6-(1-methyl-1H-benzimidazol-2-yl)-2-n-propyl-1H-benzimidazol-1-yl-methyl]biphenyl-2-carboxylic acid dihydrochloride (50 gms) is suspended in methanol (450 ml) and mixed for about 15 min. Charcoal (5.0 gms) is added, mixed for about 30 min, filtered off the charcoal through hyflow bed and washed the bed with methanol (50 ml). pH of the filtrate is adjusted to 6.5 with aqueous ammonia solution at temperature of 25° C.-35° C. Temperature of the mass is raised, maintained for 1 hr at 50° C.-55° C., Cooled and maintained for 6 hrs at 0-5° C. Product is filtered, wet cake is washed with water (2×100 ml) and finally with methanol (100 ml). Dried the wet cake at temperature of 75° C.-85° C. till becomes constant weight.

Dry weight of Telmisartan is 36 gms (Yield: 82.2%)

IR, DSC confirms the product as polymorphic Form-A

We claim:

1. A process for the preparation of Telmisartan comprising:
condensing 4-Methyl-2-n-propyl-11H-benzimidazole-6-carboxylic acid with N-Methyl-O-phenylenediamine dihydrochloride in the presence of polyphosphoric acid (PPA) yields 4-methyl-6 (1-methyl benzimidazol-2-yl)-2-n-propyl 1H-benzimidazole;
treating 4-methyl-6-(1-methyl benzimidazol-2-yl)-2-n-propyl-1H-benzimidazole with 4'-(bromomethyl)-2-biphenyl-2-carboxylate in presence of a base in an organic solvent followed by treatment with mineral acid yields acid addition salt of 4'-[4-Methyl-6-(1-methyl-1H-benzimidazol-2-yl)-2-n-propyl-1H-benzimidazol-1-1-yl-methyl]biphenyl-2-carboxylate ester;
treating 4'-[4-Methyl-6-(1-methyl-1H-benzimidazol-2-yl)-2-n-propyl-1H-benzimidazol-1-yl-methyl]biphenyl-2-carboxylate ester acid addition salt with aqueous hydrochloric acid yields Telmisartan dihydrochloride; and
converting Telmisartan dihydrochloride to Telmisartan.

2. The process as claimed in claim 1, wherein 4-methyl-6 (1-methyl benzimidazol-2-yl)-2-n-propyl 1H-benzimidazole is purified by dissolving the crude in methanol and isolating the product by adding water.

3. The process as claimed in claim 1, wherein 4'-(bromomethyl)-2-biphenyl-2-carboxylate is its methyl ester or tert.butyl ester.

4. The process as claimed in claim 1, wherein condensation of 4-methyl-6-(1-methyl benzimidazol-2-yl)-2-n-propyl-1H-benzimidazole with 4'-(bromomethyl)-2-biphenyl-2-carboxylate is carried out in acetone, methyl ethyl ketone or methyl isobutyl ketone.

5. The process as claimed in claim 1, wherein condensation of 4-methyl-6-(1-methyl benzimidazol-2-yl)-2-n-propyl-1H-benzimidazole with 4'-(bromomethyl)-2-biphenyl-2-carboxylate is carried out in presence of sodium hydroxide or potassium hydroxide.

6. The process as claimed in claim 1, wherein the obtained Telmisartan is polymorph Form-A characterized by the following:
has a melting temperature of about 269 degrees C.; and
has an IR spectrum with characteristic band at 815 $cm^{-1}$.

* * * * *